(12) United States Patent
Levin

(10) Patent No.: US 6,291,506 B1
(45) Date of Patent: Sep. 18, 2001

(54) METHOD OF REDUCING RETINAL GANGLION CELL DEGENERATION

(75) Inventor: Leonard A Levin, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/366,525

(22) Filed: Aug. 3, 1999

Related U.S. Application Data

(60) Provisional application No. 60/095,261, filed on Aug. 4, 1998.

(51) Int. Cl.$^7$ .................................................. A61K 31/40
(52) U.S. Cl. .......................... 514/411; 514/912; 514/913
(58) Field of Search .................................. 514/411, 912, 514/913

(56) References Cited

U.S. PATENT DOCUMENTS

| | | |
|---|---|---|
| 4,503,067 | 3/1985 | Wiedemann . |
| 4,760,085 | 7/1988 | Bartsch . |
| 5,405,863 | 4/1995 | Barone . |
| 5,597,809 | 1/1997 | Dreyer . |

FOREIGN PATENT DOCUMENTS

| | | |
|---|---|---|
| WO 93 16701 A | 9/1993 | (WO) . |
| WO 94 13275 A | 6/1997 | (WO) . |
| WO 99 00129 A | 1/1999 | (WO) . |

OTHER PUBLICATIONS

Glovinsky Y et al., "Retinal Ganglion cell Loss Is Size Dependent In Experimental Glaucoma" *Investigative Ophthalmology & Visual Science*, US, Hagerstown, MD, vol. 32, No. 3, Mar. 1, 1991, pp. 484–491, XP000613326, ISSN: 0146–0404.

Rosenbaum, et al., "Carvedilol, a Novel B–Blocker, Affords Protection From Transient Retinal Ischemia," *Abstract*, UW—Vision Research Group, vol. 40, No. 4 2536–B411 (1999).

Lyski, et al., "Neuroprotective Activities of Carvedilol and a Hydroxylated Derivative," *Biochemical Pharmacology*, vol. 56, 1645–1656 (1998).

Lyski, et al., "Neuroprotective Effects of Carvedilol, a New Antihypertensive Agent, in Cultured Rat Cerebellar Neurons and in Gerbil Global Brain Ischemia," *Stroke*, vol. 23, No. 11 (1992).

Merté, Vasoactivity and IOP Reducing Effect of Beta Blockers, *Klin. Mb. Augenheilk*, 189, 396–397 (1986).

Yue, et al., "Carvedilol, a New Antihypertensive Drug with Unique Antioxidant Activity: Potential Role in Cerebroprotection," *Annals New York Acadamy of Sciences*.

*Primary Examiner*—Zohreh Fay
(74) *Attorney, Agent, or Firm*—Michael Best & Friedrich LLP; Jill A. Fahrlander

(57) ABSTRACT

Disclosed is a method of reducing intraocular pressure or retinal ganglion cell death caused by specific reactive oxygen species by delivering carvedilol or a derivative or metabolite thereof having beta-adrenergic antagonist activity or specific reactive oxygen species scavenging activity to the retinal ganglion cells of a subject having or at risk of developing glaucomatous or other optic neuropathy.

14 Claims, No Drawings

METHOD OF REDUCING RETINAL GANGLION CELL DEGENERATION

CROSS-REFERENCE TO RELATED APPLICATIONS

This application claims priority to U.S. Provisional Application Serial No. 60/095,261, filed Aug. 4, 1998, which is incorporated by reference herein.

STATEMENT REGARDING FEDERALLY SPONSORED RESEARCH OR DEVELOPMENT

This invention was supported by United States government funds in the form of grant NIH K11-EY00340 awarded by the National Institutes of Health.

BACKGROUND OF THE INVENTION

Glaucomatous optic neuropathy, the second leading cause of permanent blindness in the United States, is associated with an increased rate of retinal ganglion cell death. Epidemiological studies have shown that elevated intraocular pressure (IOP) is the most common risk factor associated with primary open angle glaucoma, the most common form of the disease. It is hypothesized that chronically elevated IOP creates a pressure gradient along the course of exiting optic nerve axons, and thereby interferes with axonal transport or circulation, ultimately causing death of retinal ganglion cells.

Because there is a high correlation between glaucomatous optic neuropathy and increased IOP, strategies for treating glaucomatous optic neuropathy have been directed almost exclusively toward methods of reducing IOP. Currently, the pharmacological treatment of choice consists primarily of the topical application of ocular hypotensive agents (Sugrue, *Pharmacol. Ther.* 43:91–138, 1989).

Despite their widespread use in the treatment of glaucomatous optic neuropathy, ocular hypotensive agents are not effective in treating a large percentage of people with glaucomatous optic neuropathy. Many people with glaucomatous optic neuropathy have a normal IOP. From 30–50% of people with open angle glaucoma do not initially have ocular hypertension, and as many as 15–50% of patients with glaucomatous optic neuropathy do not have elevated IOP. Therefore, considerable effort has been directed toward developing suitable methods for treating glaucomatous optic neuropathy in patients with normal or high IOP, as well as for treating several other optic neuropathies that are not associated with increased IOP. The absence of increased IOP in certain glaucomatous optic neuropathy patients suggests that there is at least one mechanism other than elevated intraocular pressure that contributes to the optic neuropathy associated with glaucomatous optic neuropathy (Levin, *Current Opinion in Ophthalmology* 8:9–15, 1997; Levin, *Mediguide to Ophthalmology* 8:1–5, 1999).

Knowledge of mechanisms responsible for natural and experimental optic neuropathy, including axonal transection, optic nerve crush and optic nerve ischemia, may facilitate development of suitable treatments for glaucomatous optic neuropathy and other optic neuropathies affecting the axons of retinal ganglion cells, including ischemic optic neuropathy, inflammatory optic neuropathy, compressive optic neuropathy, and traumatic optic neuropathy. Each of these conditions likely causes apoptosis. The mechanism responsible for initiating apoptosis in retinal ganglion cells has not been unequivocably established. However, it is speculated that decreased retrograde transport of neurotropic factors, decreased levels of endogenous ocular neurotrophins, or any one of several other mechanisms may trigger apoptosis.

U.S. Pat. No. 5,667,968, incorporated herein by reference, discloses the use of ciliary neurotrophic factor (CNTF) and other neurotrophic factors to prevent injury or death of retinal neurons. The neurotrophic factors may be administered intraocularly or into the vitreous of the eye.

Neurotrophin deprivation may initiate at least one of several cytotoxic cellular mechanisms. Such mechanisms include, without limitation, excitotoxicity, reactions catalyzed or signaled by reactive oxygen species, mitochondrial depolarization, mitochondrial release of apoptosis-inducing factors, and elevation of intracellular calcium concentrations to toxic levels.

Therapeutic agents useful in inhibiting cell death induced or initiated by cytotoxic mechanisms have been identified in preliminary studies using model systems. For example, glutamate receptor antagonists (including dextromethorphan, NMDA antagonists, and aspartate antagonists) may be used to protect against excitotoxicity. Reactive oxygen species scavengers (e.g., superoxide dismutase and catalase) and antioxidants (e.g., vitamin E and D-mannitol) may be used to quench specific reactive oxygen species. Calcium channel blockers such as dihydropyridines may be used to reduce toxic intracellular calcium levels.

What is needed in the art is a new method for treating glaucomatous optic neuropathy and other eye diseases affecting the retinal ganglion cells.

BRIEF DESCRIPTION OF THE SEVERAL VIEWS OF THE DRAWINGS

Not applicable.

BRIEF SUMMARY OF THE INVENTION

The present invention provides a method for reducing retinal ganglion cell death in a subject comprising the steps of:

(a) providing at least one carbazolyl-(4)-oxypropanolamine compound selected from the group consisting essentially of the compounds of Formula 1:

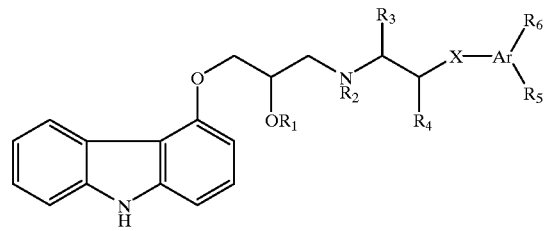

wherein:

$R_1$ is hydrogen, lower alkanoyl of up to 6 carbon atoms or aroyl selected from benzoyl and naphthoyl;

$R_2$ is hydrogen, lower alkyl of up to 6 carbon atoms or arylalkyl selected form benzyl, phenylethyl and phenylpropyl;

$R_3$ is hydrogen or lower alkyl of up to 6 carbon atoms;

$R_4$ is hydrogen or lower alkyl of up to 6 carbon atoms, or when X is oxygen, $R_4$ together with $R_5$ can represent —$CH_2$—O—;

X is a valency bond, —$CH_2$, oxygen or sulfur;

Ar is selected from phenyl, naphthyl, indanyl and tetrahydronaphthyl;

$R_5$ and $R_6$ are individually selected from hydrogen, fluorine, chlorine, bromine, hydroxyl, lower alkyl of up to 6 carbon atoms, a —$CONH_2$-group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or $R_5$ and $R_6$ represent together methylenedioxy; and pharmaceutically acceptable salts thereof;

(b) delivering a therapeutically effective amount of the compound of step (a) to at least a portion of the subject's retinal ganglion cells (RGC).

In a preferred embodiment, the compound of step (a) is carvedilol (1-(carbazol-4-yloxy-3-[[2-(o-methoxyphenoxy) ethyl]amino-2-propanol), which has the following structure:

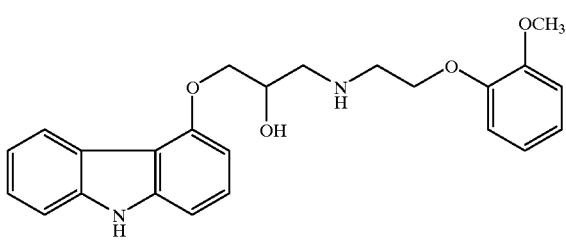

Most conveniently, the compound of step (a) is delivered by topical application to the eye, wherein the compound is supplied as a pharmaceutical formulation comprising the compound in a therapeutically effective concentration and a pharmaceutically acceptable carrier that may suitably be administered to the subject as an eyedrop. More preferably still, compound is delivered in a sustained-release formula.

Another aspect of the invention is a pharmaceutical formulation for reducing retinal ganglion cell death in a subject by the method of the present invention, the formulation comprising a compound having the formula

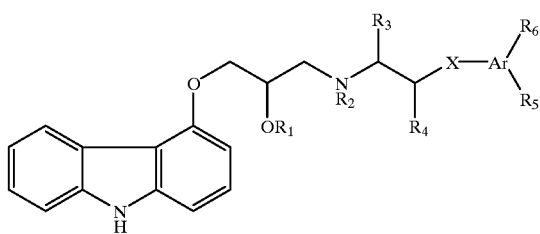

wherein:

$R_1$ is hydrogen, lower alkanoyl of up to 6 carbon atoms or aroyl selected from benzoyl and naphthoyl;

$R_2$ is hydrogen, lower alkyl of up to 6 carbon atoms or arylalkyl selected form benzyl, phenylethyl and phenylpropyl;

$R_3$ is hydrogen or lower alkyl of up to 6 carbon atoms;

$R_4$ is hydrogen or lower alkyl of up to 6 carbon atoms, or when X is oxygen, $R_4$ together with $R_5$ can represent —$CH_2$—O—;

X is a valency bond, —$CH_2$, oxygen or sulfur;

Ar is selected from phenyl, naphthyl, indanyl and tetrahydronaphthyl;

$R_5$ and $R_6$ are individually selected from hydrogen, fluorine, chlorine, bromine, hydroxyl, lower alkyl of up to 6 carbon atoms, a —$CONH_2$-group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or $R_5$ and $R_6$ represent together methylenedioxy; and pharmaceutically acceptable salts thereof; in a therapeutically effective concentration and a pharmaceutically acceptable carrier. Preferably, the compound is carvedilol.

It is an object of the invention to provide a method for reducing retinal ganglion cell death in a subject susceptible to an increased rate of retinal ganglion cell death.

It is a further object of the invention to provide a pharmaceutical formulation for use in reducing retinal ganglion cell death in a subject susceptible to increased retinal ganglion cell death.

It is an advantage that the method of the invention employs an agent effective in reducing intraocular pressure or scavenging specific reactive oxygen species.

It is an advantage that at least one species of carbazolyl-(4)-oxy-propanolamine compounds (carvedilol) has already been shown to be relatively safe and nontoxic for humans in other clinical indications.

Additional objects, advantages, and features of the invention will become apparent upon review of the specification.

DETAILED DESCRIPTION OF THE INVENTION

As discussed in U.S. Ser. No. 60/095,261, retinal ganglion cell (RGC) death associated with conditions such as glaucomatous optic neuropathy may be caused by more than one mechanism, including, but not limited to, excitotoxicity, reactive oxygen species-signaled or catalyzed reactions, or high intracellular calcium concentrations. In U.S. Ser. No. 60/095,261, Applicants showed that certain tested specific reactive oxygen species scavengers can reduce RGC death in vitro, and proposed that carvedilol may also be effective in reducing RGC death.

Carvedilol is a carbazolyl-(4)-oxypropanolamine having multiple pharmacological activities, as disclosed in U.S. Pat. Nos. 4,503,067 and 5,405,863, which are incorporated by reference herein. Carvedilol and related compounds have been shown to be potent antioxidants. In addition, carvedilol is a nonselective β-adrenoreceptor antagonist with a vasodilating activity. These properties make carvedilol potentially useful in treating mild to moderate essential hypertension, myocardial necrosis, arrhythmia, and congestive heart failure. The activities of carvedilol are reviewed in Feuerstein et al., Protective Effects of Carvedilol in the Myocardium, Am. J. Cardiol. 80(11A): 41L–45L (1997) and Dunn et al., Carvedilol: A Reappraisal of its Pharmacological Properties and Therapeutic Use in Cardiovascular Disorders, Drugs 54(1) 161–85 (1997), both of which are incorporated by reference herein.

Reactive oxygen species (ROS) have been implicated in the pathogenesis of a large number of human diseases, including disorders as disparate as cancer, atherosclerosis, arthritis, and neuro-degenerative disorders. Although the use of reactive oxygen species scavengers in the prevention and treatment of such conditions is often suggested, it has become clear that simply administering a reactive oxygen species scavenger does not uniformly afford protection nor result in successful treatment of these diseases. The failure of generalized ROS scavenging in treating diseases is due to many factors, discussed below.

There are multiple species of ROS, which have different physical, chemical, and bioactive properties. An abbreviated listing of clinically important ROS includes superoxide anion ($O_2^-$), hydrogen peroxide ($H_2O_2$), hydroxyl radical (OH•), nitric oxide (NO), peroxynitrite ($ONOO^-$), hypochlorous ion (HOCl), and several others.

A given ROS scavenger may reduce the levels of only one or two ROS, but have no effect on or actually increase levels of certain other ROS. For example, ascorbate (vitamin C) may increase the levels of hydroxyl radical by maintaining iron or copper in their reduced states, thereby allowing the Fenton reaction to produce hydroxyl radical.

Different cells exhibit differential susceptibility to specific ROS. Presumably, this is a consequence of the variability in the type and level of intracellular defense mechanisms against ROS that different cell types have. Examples of intracellular defense mechansims include superoxide dismutase (of which there are at least 3 types), catalase, myeloperoxidase, reduced glutathione, glutathione peroxidase, thioredoxin reductase, and many other defense mechanisms. Therefore, a certain ROS may be injurious for one type of cell, but leave an adjacent cell unaffected.

A particular disease process may cause an increase in one or more ROS in a certain cell type, whereas a second disease process may cause an increase in a different ROS. For example, injury to the axon of a neuron, which causes decreased retrograde transport of neurotrophic factors or other effects, may have a very different intracellular action than excitotoxic damage mediated by cell body hypoxia, which may cause dramatic increases in nitric oxide-mediated damage. Therefore, an ROS scavenger that protects a specific cell type affected by a condition that causes harm to the axonal region of the cell may be ineffective in the same cell type affected by a condition that damages a different portion of the cell (e.g., the cell body) (Schwartz, et al. 1999 *Molec. Med. Today*, in press).

The data provided in the Examples below demonstrate the idiosyncratic and unpredictable nature of ROS scavenger-mediated protection of cells. The Examples below show that carvedilol protects axotomized RGC against cell death, but protects non-RGC neuronal cells to a lesser extent. Because axonal injury to RGC is implicated in most optic neuropathies, including glaucomatous optic neuropathy, inflammatory optic neuropathy, compressive optic neuropathy, and traumatic optic neuropathy, it is reasonably expected that the RGC of an individual experiencing or at risk for developing one of these conditions will be protected by treating the individual with carvedilol.

Carvedilol is a member of a class of compounds having the general formula (Formula 1):

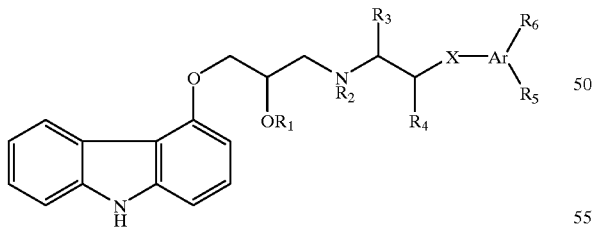

wherein:
R$_1$ is hydrogen, lower alkanoyl of up to 6 carbon atoms or aroyl selected from benzoyl and naphthoyl;
R$_2$ is hydrogen, lower alkyl of up to 6 carbon atoms or arylalkyl selected form benzyl, phenylethyl and phenylpropyl;
R$_3$ is hydrogen or lower alkyl of up to 6 carbon atoms;
R$_4$ is hydrogen or lower alkyl of up to 6 carbon atoms, or when X is oxygen, R$_4$ together with R$_5$ can represent —CH$_2$—O—;

X is a valency bond, —CH$_2$, oxygen or sulfur;
Ar is selected from phenyl, naphthyl, indanyl and tetrahydronaphthyl;
R$_5$ and R$_6$ are individually selected from hydrogen, fluorine, chlorine, bromine, hydroxyl, lower alkyl of up to 6 carbon atoms, a —CONH$_2$-group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or R$_5$ and R$_6$ represent together methylenedioxy. It is reasonably expected that members of this class of compounds, and pharmaceutically acceptable salts thereof, may have protect RGC by reducing IOP or by scavenging specific oxygen free radicals.

Using the teachings disclosed herein, one of ordinary skill in the art could easily screen Formula 1 compounds to assess the ability of each to protect RGC. Therefore, it is expected that any Formula I compound having IOP reducing activity or that protects RGC by scavenging specific reactive oxygen species could be used in the practice of the present invention.

Accordingly, the present invention includes a method for reducing retinal ganglion cell death in a subject, comprising the steps of:
(a) providing at least one compound selected from the group consisting essentially of the compounds of Formula 1:

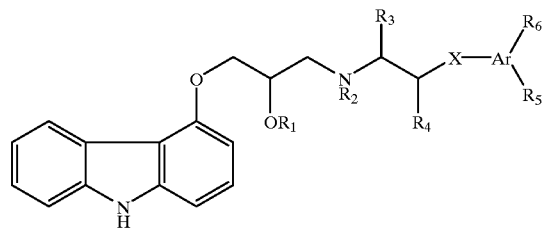

wherein:
R$_1$ is hydrogen, lower alkanoyl of up to 6 carbon atoms or aroyl selected from benzoyl and naphthoyl;
R$_2$ is hydrogen, lower alkyl of up to 6 carbon atoms or arylalkyl selected form benzyl, phenylethyl and phenylpropyl;
R$_3$ is hydrogen or lower alkyl of up to 6 carbon atoms;
R$_4$ is hydrogen or lower alkyl of up to 6 carbon atoms, or when X is oxygen, R$_4$ together with R$_5$ can represent —CH$_2$—O—;
X is a valency bond, —CH$_2$, oxygen or sulfur;
Ar is selected from phenyl, naphthyl, indanyl and tetrahydronaphthyl;
R$_5$ and R$_6$ are individually selected from hydrogen, fluorine, chlorine, bromine, hydroxyl, lower alkyl of up to 6 carbon atoms, a —CONH$_2$-group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or R$_5$ and R$_6$ represent together methylenedioxy; and pharmaceutically acceptable salts thereof;
(b) delivering a therapeutically effective amount of the compound of step (a) to at least a portion of the subject's retinal ganglion cells (RGC).

In a preferred embodiment, the compound of step (a) is carvedilol (1-(carbazol-4-yloxy-3-[[2-(O-methoxyphenoxy)

ethyl]amino-2-propanol), which has the following structure:

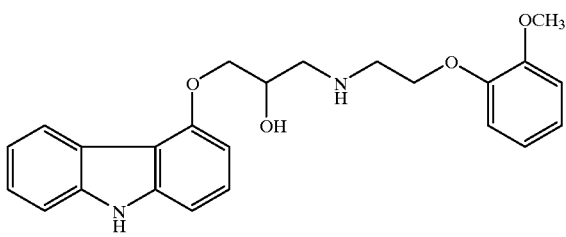

The delivery of the Formula 1 compounds to the RGC may be achieved by any means that allows delivery of carvedilol or a metabolite retaining the IOP reducing or RCG protecting activity to the RGC. Most conveniently, the Formula 1 compound could be delivered by formulating it as an eyedrop, more preferably still as a sustained-release eye drop. Preferably, the formula 1 compound is suspended in an agent which will increase the corneal contact time with and penetration by the Formula 1 compound. Such agents include gellan gum and xanthum gum as disclosed in Meseguer et al., Gamma Scintigraphic Comparison of Eye-drops Containing Pilocarpine in Healthy Volunteers, J. Ocular. Pharm. Ther. 12(4):481–8 (1996) and Nelson et al., Ocular Tolerability of Timilol in Gelrite in Young Glaucoma Patients, J. Am. Optom. Assoc. 67(11):659–63 (1996), herein incorporated by reference. Alternatively, carvedilol may be formulated as a sustained-release delivery system to be placed under the eyelid, conjunctiva, sclera, retina, optic nerve sheath, or in an intraocular or intraorbitol location. Depending on the delivery site chosen, the carvedilol could be formulated on a solid or semisolid support. Other possible delivery modes include oral, intravaginal, rectal, transdermal, intravenous, or any other method of drug delivery known to the art.

By a "therapeutically effective amount" it is meant an amount of a Formula 1 compound that is sufficient to reduce intraocular pressure or protect RGC against specific reactive oxygen species. Of course, what constitutes a therapeutically effective amount will depend on a variety of factors, including, for example, the size, age, and condition of the subject, as well as on the mode of delivery. It is well within the ability of one of ordinary skill in the art to determine effective dosages.

Preferably, the subject is a human experiencing or at risk of developing a condition that is associated with reactive oxygen species-mediated RGC death, including glaucomatous optic neuropathy, ischemic optic neuropathy, inflammatory optic neuropathy, compressive optic neuropathy, and traumatic optic neuropathy. All of the above-mentioned conditions are associated with damage to the axonal region of RGC, as opposed to the cell body. It is possible that the Formula 1 compound may be neuroprotective of central nervous system cells affected by axonal diseases, including spinal cord injury and peripheral neuropathies.

It is reasonable to expect that the more RGC that the Formula 1 compound contacts, the more pronounced its protective effect. Preferably, the method of the present invention allows the Formula 1 compound to contact at least about 25%, 50% or even as many as 95 or 100% of the RGC.

Preferably, contacting the RGC with the Formula 1 compound will reduce cell death by at least about 50%. However, it is expected a reduction of RGC death of only 25%, 10% or 5% will extend the vision of the treated subject. In a human subject, a reduction in retinal ganglion cell death may be estimated by extrapolation of functional and structural assays.

Functional assays involve evaluating changes in visual function over time, specifically, visual acuity and visual fields. It is reasonably expected that a reduction in the rate of RGC death following initiation of Formula 1 compound treatment may be correlated with a reduction in the rate of loss of visual function over time. Structural assays involve visualizing or measuring the optic nerve head or the optic nerve fiber layer with an ophthalmoscope or other device to assess optic disc atrophy, disc cupping, or loss of nerve fibers.

When delivered to subjects having increased intraocular pressure by the method of the present invention, the Formula 1 compound is expected to reduce IOP by at least about 25% of the difference between the IOP in the untreated subject and the upper limit of the normal range for IOP. Preferably, this reduction is 50% or more. Most preferably, the IOP of a subject treated with Formula 1 compound will fall within the normal range.

In a preferred embodiment, a therapeutically effective amount of the formula 1 compound will be administered topically to the eye of a human subject exhibiting symptoms of or at risk for developing a disease affecting retinal ganglion cells. Most preferably, carvedilol is administered in a formula that allows sustained release of the carvedilol over time (see e.g. Remington's Pharmaceutical Sciences, 14th Ed. 1970, incorporated herein by reference). Recently, ganciclovir and pilocarpine have been incorporated into intraocular implants or on a support placed under the eyelid for sustained release delivery of these agents to the eye. Other examples of formulations for sustained release of therapeutic agents topically applied to the eye may be found in Joshi, J. Ocul. Pharmacol. 10(1):29–45 (1994), McCalden et al., Experientia 46(7):713–15 (1990), Feist et al., J. Cataract Refract. Surg. 21(2):191–95 (1995), Cheng et al., Invest. Opthalmol. Vis. Sci. 36(2):442–53 (1995) and Chetoni et al., J. Ocul. Pharmacol. Ther. 1293):245–52 (1996). The foregoing references are herein incorporated by reference.

The method of the present invention is preferably used to treat a subject with a disorder affecting the axons of retinal cell ganglion cells, including, but not limited to glaucomatous optic neuropathy, ischemic optic neuropathy, inflammatory optic neuropathy, compressive optic neuropathy, and traumatic optic neuropathy.

The following nonlimiting examples are intended to be purely illustrative.

EXAMPLES

Animals

All experiments were performed in accordance with ARVO, institutional, federal, and state guidelines regarding animal research.

Ganglion Cell Labeling and Culture

Retinal ganglion cells were labeled and cultured using previously described methods (Levin, Investigative Ophthalmology Vis. Sci. 37:2744–2749, 1996). Briefly, ganglion cells were retrogradely labeled by stereotactic injection of the fluorescent tracer DiI dissolved in dimethylformamide into the superior colliculi of anesthetized postnatal day 2–4 Long-Evans rats. At postnatal day 7–9 the animals were sacrificed by decapitation, the eyes enucleated, and the retinas dissected free in Hank's balanced salt solution (HBSS). After two incubations in HBSS containing papain (12.5 U/ml) for 30 minutes at 37°, the retinas were gently triturated with a Pasteur pipette and plated on poly-L-lysine-coated 96-well flat-bottom tissue culture plates (0.32 cm$^2$ surface area per well) at a density of approximately 2000 cells/mm$^2$. The cells were cultured in Eagle's minimal essential medium (MEM) with methylcellulose (0.7%), glutamine (2 mM), gentamicin (1 µg/ml), glucose (22.5 mM final concentration), and prescreened fetal calf serum (5%). Some suspensions were plated onto poly-L-lysine-coated glass cover slips in 24-well plates to allow microphotographs of labeled cells.

Ganglion Cell Identification and Counting

Retinal ganglion cells were identified by the presence of retrogradely transported cytoplasmic DiI, which appears red-orange when viewed with rhodamine filters under epifluorescence. Cell viability was determined by metabolism of calcein-AM, producing green fluorescence when viewed with fluorescein filters. Briefly, cells were incubated in a 1 µM solution of calcein-AM in PBS for 20 minutes, after which the medium was replaced with fresh PBS, and the total number of living ganglion cells counted in each well. Wells were counted in triplicate; in some large experiments, counting was in duplicate.

Effect of different ROS on RGC Survival.

The effect of various ROS on RGC survival was determined by exposing the cells to the ROS. Superoxide anion was generated using the xanthine (X)/xanthine oxidase (XO) $O_2^-$ generating system. $H_2O_2$ was added directly. RGC survival was measured 24 hours after axotomy as described above.

| Treatment | RGC survival |
| --- | --- |
| Control (vehicle) | 38 ± 2% |
| 0.0001% $H_2O_2$ | 41 ± 1% |
| 100 µM X/20 U/L XO | 0 ± 0% |

These results demonstrate that RGC are extremely sensitive to the X/XO system, but are relatively insensitive to $H_2O_2$.

Effect of $H_2O_2$ on RGC's and non-RGC Retinal neurons.

To assess the effect of $H_2O_2$ on RGC's and non-RGC retinal neuron survival, cells were treated with a control or $H_2O_2$ and the survival was assessed as described above.

| Treatment | RGC | Non-RGC |
| --- | --- | --- |
| Control | 43 ± 1% | 14 ± 0.2% |
| 0.0001% $H_2O_2$ | 37 ± 0.5% | 1 ± 0.2% |

These results show the differential sensitivity of RGC and non-RGC neuronal cells to a common ROS.

Efficacy of Various ROS Scavengers in Increasing RGC Survival in Response to ROS Challenge Several ROS scavengers were tested for their protective effect on RGC cells in the presence or absence of challenge. The following agents were tested: Cu(II)bis-3,5-diisopropyl-salicylate) (CuCIPS); 4,5-dihydroxy-1,3-benzene disulfonic acid (TIRON); and Mn(III) tetrakis (1-methyl-4-pyridyl porphyrin pentachloride) (MnTMPyP).

| Treatment | No challenge | X/XO challenge |
| --- | --- | --- |
| Control | 38 ± 2 | 0 ± 0 |
| 25 µM CuDIPS | 66 ± 3 | 0 ± 0 |
| 10 mM TIRON | 57 ± 1 | 0 ± 0 |
| 50 µM MnTMPyP | 57 ± 3 | 47 ± 1 |

These results show that there is considerable variability in the protection afforded by ROS scavengers.

Efficacy of ROS Scavengers as a Function of Type of Insult to non-RGC Retinal Neuron Cells The ability of ROS scavengers to protect non-RGC retinal neurons against injury was evaluated by treating cells with staurosporine (1 µM), which induces apoptosis, or with $H_2O_2$, which induces oxidative stress, and measuring cell survival.

| Treatment | No challenge | Staurosporine | $H_2O_2$ |
| --- | --- | --- | --- |
| Control | 31 ± 3 | 21 ± 2 | 7 ± 0.4 |
| Catalase (500 U/ml) | 54 ± 4 | 21 ± .2 | 38 ± 3 |

The non-RGC cells are much more sensitive to staurosporine (SS) than to $H_2O_2$. Catalase enhanced survival of cells treated with $H_2O_2$, but not survival of cells treated with staurosporine Relative Protective Effect of Carvedilol on RGC and non-RGC Retinal Neurons as a Function of Insult.

The effect of carvedilol on RGC and non-RGC retinal neuron survival was tested on untreated axotomized cells or on axotomized cells treated with staurosporine by measuring cell survival. In addition, both cell types were treated with dithiothreitol (DTT).

| Treatment | RGC | Non-RGC |
| --- | --- | --- |
| Axotomy alone | 4.8 ± 2.4 | 4.6 ± 0.7 |
| Carvedilol (10 µM) | 50 ± 8.9 | 7.0 ± 1.9 |
| SS (1 µM) | 0 ± 0 | 0 ± 0 |
| Carvedilol +ss | 0 ± 0 | 0 ± 0 |
| DTT (200 µM) | 89 ± 0.6 | 69 ± 11 |

Carvedilol protects RGC, but not non-RGC neuronal cells. The RGC protection by carvedilol is not successful when given a different kind of injury (inducing apoptosis with staurosporine). Furthermore, this protection with carvedilol differs qualitatively from other agents, e.g. the thiol reducing agent DTT, which protects both axotomized RGC's and non-RGC's.

The invention is not limited to the exemplified embodiments, but is intended to encompass all such modifications and variations as come within the scope of the following claims.

What is claimed is:

1. A method for reducing axonally-mediated retinal ganglion cell death in a subject having an axonally-mediated condition selected from the group consisting of pressure-independent glaucomatous optic neuropathy, ischemic optic neuropathy, inflammatory optic neuropathy, compressive optic neuropathy, and traumatic optic neuropathy, comprising the steps of:

(a) providing at least one compound selected from the group consisting essentially of the compounds of Formula 1:

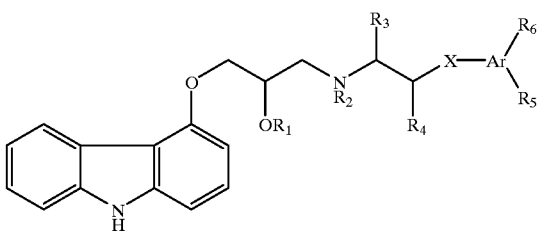

Wherein:
- $R_1$ is hydrogen, lower alkanoyl of up to 6 carbon atoms or aroyl selected from benzoyl and naphthoyl;
- $R_2$ is hydrogen lower alkyl of up to 6 carbon atoms or arylalkyl selected from benzyl, phenylethyl and phenylpropyl;
- $R_3$ is hydrogen or lower alkyl of up to 6 carbon atoms;
- $R_4$ is hydrogen or lower alkyl of up to 6 carbon atoms, or when X is oxygen, $R_4$ together with $R_5$ can represent —$CH_2$—O—;
- X is a valency bond, —$CH_2$, oxygen or sulfur;
- Ar is selected from phenyl, naphthyl, indanyl and tetrahydronaphthyl;
- $R_5$ and $R_6$ are individually selected from hydrogen, fluorine, chlorine, bromine, hydroxyl, lower alkyl of up to 6 carbon atoms, a —$CONH_2$-group, lower alkoxy of up to 6 carbon atoms, benzyloxy, lower alkylthio of up to 6 carbon atoms, lower alkysulphinyl of up to 6 carbon atoms and lower alkylsulphonyl of up to 6 carbon atoms; or $R_5$ and $R_6$ represent together methylenedioxy; and pharmaceutically acceptable salts thereof; and (b) delivering a therapeutically effective amount of the compound of step (a) to at least a portion of the subject's retinal ganglion cells (RGC).

2. The method of claim 1, wherein the compound of step (a) is carvedilol, or a pharmaceutically acceptable salt thereof.

3. The method of claim 1, wherein the compound of step (a) is supplied as a formulation comprising the compound in a therapeutically effective concentration, and a pharmaceutically acceptable carrier.

4. The method of claim 1, wherein the compound of step (a) is delivered to the retinal ganglion cells by applying the compound of step (a) to the eye of the subject.

5. The method of claim 1, wherein the compound of step (a) is delivered as an eyedrop to the cornea.

6. The method of claim 3, wherein the formulation is a sustained release formulation.

7. The method of claim 3, wherein the compound of step (a) is formulated on a solid or semisolid support, wherein delivery is accomplished by placing the support in a region of the eye selected from the group consisting of the eyelid, conjunctiva, sclera, retina, optic nerve sheath, an intraocular location and an intraorbital location.

8. The method of claim 5, wherein the eyedrop further comprises an agent that increases corneal contact time with or penetration by the compound of step (a).

9. The method of claim 1, wherein the subject is a human.

10. The method of claim 1, wherein the subject has pressure-independent glaucomatous optic neuropathy.

11. The method of claim 1, wherein the intraocular pressure of the treated subject is reduced relative to the intraocular pressure in the absence of treatment with compound of step (a).

12. The method of claim 1, wherein compound of step (a) protects the cells against at least one reactive oxygen species.

13. The method of claim 1, wherein the compound of step (a) reduces intraocular pressure and protects the cells against at least one reactive oxygen species.

14. The method of claim 1, wherein the compound of step (a) is delivered orally, intravenously, sublingually, transdermally, vaginally, or rectally.

* * * * *